(12) United States Patent
Kinoshita et al.

(10) Patent No.: US 10,064,561 B2
(45) Date of Patent: Sep. 4, 2018

(54) BLOOD PRESSURE MEASUREMENT APPARATUS, BLOOD PRESSURE MEASUREMENT METHOD, AND BLOOD PRESSURE MEASUREMENT PROGRAM

(71) Applicant: OMRON HEALTHCARE Co., Ltd., Kyoto (JP)

(72) Inventors: Hiroyuki Kinoshita, Kyoto (JP); Hironori Sato, Kyoto (JP); Toshihiko Ogura, Kyto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 273 days.

(21) Appl. No.: 14/670,668

(22) Filed: Mar. 27, 2015

(65) Prior Publication Data

US 2015/0196206 A1  Jul. 16, 2015

Related U.S. Application Data

(63) Continuation of application No. PCT/JP2013/070623, filed on Jul. 30, 2013.

(30) Foreign Application Priority Data

Sep. 28, 2012  (JP) .................. 2012-217408

(51) Int. Cl.
*A61B 5/02* (2006.01)
*A61B 5/0225* (2006.01)
(Continued)

(52) U.S. Cl.
CPC ............ *A61B 5/0225* (2013.01); *A61B 5/024* (2013.01); *A61B 5/02116* (2013.01);
(Continued)

(58) Field of Classification Search
CPC ..... A61B 5/0225; A61B 5/024; A61B 5/7203; A61B 5/02225; A61B 5/02116; A61B 5/02208; A61B 7/02
See application file for complete search history.

(56) References Cited

U.S. PATENT DOCUMENTS 5,651,369 A * 7/1997 Tomita ................. A61B 5/0225
600/493
7,217,244 B2 * 5/2007 Suzuki ............... A61B 5/02444
600/481
(Continued)

FOREIGN PATENT DOCUMENTS

JP  03-049731 A  3/1991
JP  H04-236939 A  8/1992
(Continued)

OTHER PUBLICATIONS

International Search Report issued in corresponding International Application No. PCT/JP2013/070623 dated Aug. 27, 2013, and English translation thereof (4 pages).

*Primary Examiner* — Navin Natnithithadha
*Assistant Examiner* — Andrey Shostak
(74) *Attorney, Agent, or Firm* — Osha Liang LLP

(57) ABSTRACT

A CPU detects pulse waves in a pressure signal of a cuff detected during a period of reducing pressure applied by the cuff to a measurement site and acquires blood flow sound signals corresponding to blood flow sounds occurring in the pressure reduction period. Then, data for a pulse wave envelope that associates the amplitude values of the detected pulse waves with the pressurizing pressures at the pulse wave generation times, and data for a blood flow sound envelope that associates the amplitude values of the blood flow sound signals with the pressurizing pressures at the blood flow sound generation times are generated, and the data for the pulse wave envelope and the data for the blood
(Continued)

flow sound envelope are used to determine whether or not there is periodic variation in the blood pressure during the pressure reduction period.

9 Claims, 12 Drawing Sheets

(51) Int. Cl.
  *A61B 5/021*  (2006.01)
  *A61B 5/022*  (2006.01)
  *A61B 5/024*  (2006.01)
  *A61B 5/00*  (2006.01)
  *A61B 7/02*  (2006.01)

(52) U.S. Cl.
  CPC ...... *A61B 5/02208* (2013.01); *A61B 5/02225* (2013.01); *A61B 5/7203* (2013.01); *A61B 7/02* (2013.01)

(56) References Cited

U.S. PATENT DOCUMENTS

| | | | | |
|---|---|---|---|---|
| 2005/0119578 | A1* | 6/2005 | Kubo | A61B 5/0225 600/490 |
| 2005/0234314 | A1* | 10/2005 | Suzuki | A61B 5/0205 600/301 |
| 2005/0256412 | A1* | 11/2005 | Shimazu | A61B 5/022 600/500 |
| 2010/0260353 | A1* | 10/2010 | Ozawa | G10L 21/0208 381/94.3 |

FOREIGN PATENT DOCUMENTS

| | | |
|---|---|---|
| JP | H05-329112 A | 12/1993 |
| JP | H11-206724 A | 8/1999 |
| WO | 1991/17699 A1 | 11/1991 |

\* cited by examiner

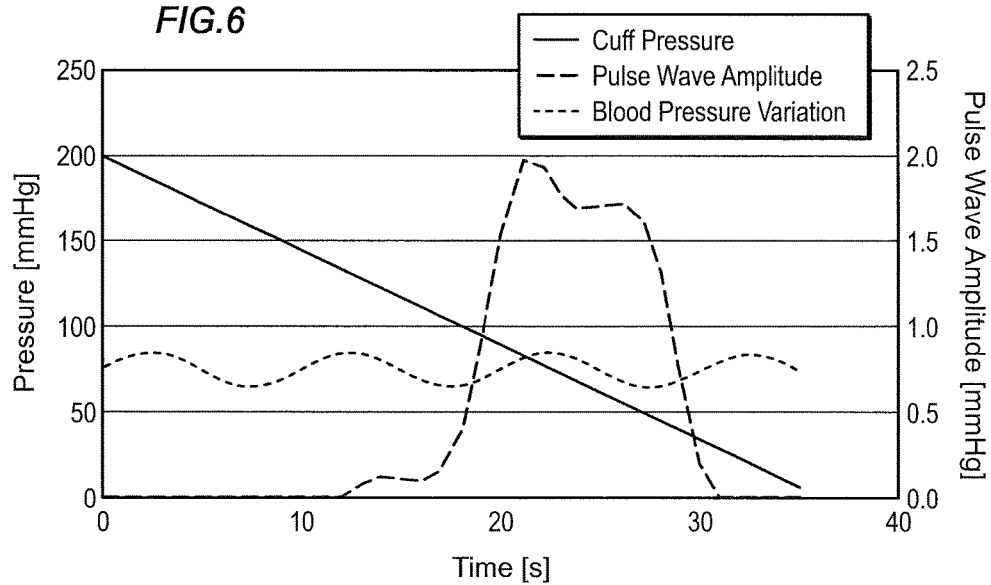
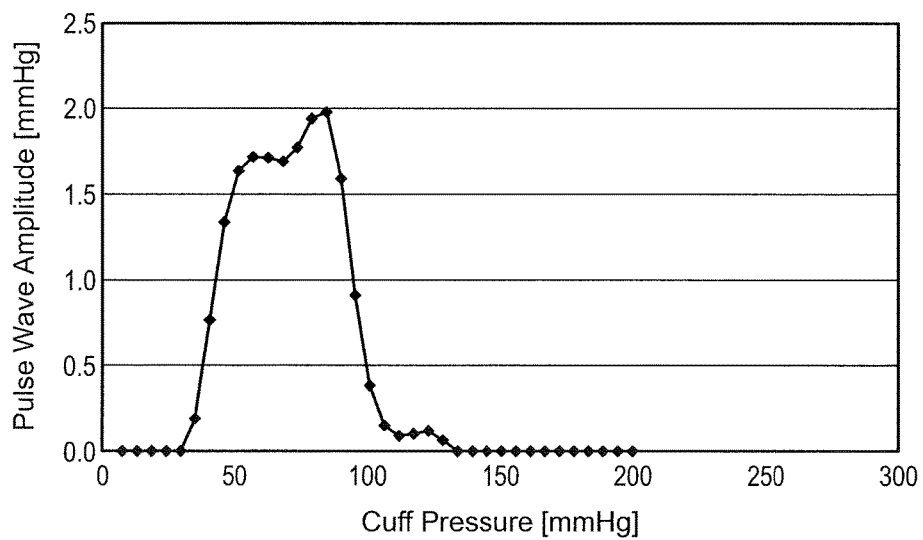

BLOOD PRESSURE MEASUREMENT APPARATUS, BLOOD PRESSURE MEASUREMENT METHOD, AND BLOOD PRESSURE MEASUREMENT PROGRAM

TECHNICAL FIELD

The present invention relates to a blood pressure measurement apparatus, a blood pressure measurement method, and a blood pressure measurement program.

BACKGROUND ART

An oscillometric (OSC) method and a K sound method are known as methods for measuring a body's blood pressure value.

The oscillometric method is a method of pressurizing an artery with a cuff, converting changes in the volume of the artery accompanying a heartbeat during a process of reducing the pressurizing pressure of the cuff (cuff pressure) into variations in pressure in the cuff (pulse wave amplitude), and calculating the blood pressure value by analyzing the variations.

Specifically, the pressure in the cuff is detected in the process of reducing the cuff pressure after the cuff pressure is increased to a value that is sufficiently greater than a systolic blood pressure value. Then, the cuff pressures and pulse waves superimposed thereon are extracted from the detected pressure in the cuff, and an envelope that stores the amplitudes of the pulse waves in a time series in pairs with the cuff pressures is created.

Based on the envelope, the cuff pressure at the time of generation of the pulse wave with the greatest amplitude is set as the average blood pressure value. Then, among the cuff pressures that are greater than the average blood pressure value, a cuff pressure at the time of generation of a pulse wave with an amplitude that is the closest in value to a predetermined percentage (e.g., about 50%) of the maximum value is set as the systolic blood pressure value. Also, among cuff pressures that are lower than the average blood pressure value, a cuff pressure at the time of generation of a pulse wave with an amplitude that is closest in value to a predetermined percentage (e.g., 60%) of the maximum value is set as the diastolic blood pressure value.

The K sound method is a method of detecting blood flow sounds (Korotkoff sounds=K sounds) of a measurement subject and determining the cuff pressure at the time when the K sounds start to occur as the "systolic blood pressure" and the cuff pressure at the time when the K sounds disappear as the "diastolic blood pressure".

In the past, blood pressure measurement apparatuses that use both an OSC method and a K sound method have been proposed, and for example, Patent Document 1 discloses a blood pressure measurement apparatus that displays a blood pressure value measured using an OSC method and a K sound method.

Also, Patent Document 2 discloses a method of using a K sound method to measure a blood pressure value and using an OSC method to evaluate a blood pressure value obtained using the K sound method in order to determine whether or not the blood pressure value is correct.

Also, Patent Document 3 discloses a system in which an envelope of pulse wave amplitudes and an envelope of K sound amplitudes are created, overlaid on one another, and output by printing.

CITATION LIST

Patent Literature

Patent Document 1: JP H11-206724A
Patent Document 2: JP H5-329112A
Patent Document 3: JP H3-49731A

SUMMARY OF INVENTION

It is known that the envelope of the pulse wave amplitudes used in blood pressure measurement according to the OSC method varies due to slight variations (e.g., respiratory variations) in blood pressure in periods that are longer than the pulse cycle of the heart. If the envelope deforms, an error will appear in the measured blood pressure value determined using the OSC method.

In Patent Documents 1 to 3, no consideration is given to measurement error caused by slight variations in the blood pressure, and the measurement error cannot be reduced.

The influence that this type of slight variation in blood pressure has on blood pressure measurement can be reduced by raising the accuracy of measuring the pressure in the cuff. However, raising the accuracy of measuring the pressure in the cuff increases the cost of the apparatus and increases the amount of time needed for blood pressure measurement.

Therefore, one or more embodiments of the claimed invention provide a blood pressure measurement apparatus, a blood pressure measurement method, and a blood pressure measurement program, according to which it is possible to prevent a decrease in the blood pressure measurement accuracy caused by slight variations in the blood pressure, without increasing the accuracy of measuring the pressure in the cuff.

A blood pressure measurement apparatus according to one or more embodiments of the claimed invention includes: a cuff configured to be attached at a measurement site of a body; a pressurizing pressure adjustment unit configured to change a pressurizing pressure applied by the cuff to the measurement site; a pressure detection unit configured to detect pressure in the cuff during a period of changing the pressurizing pressure; a pulse wave detection unit configured to detect pulse waves in a cuff pressure signal that is a signal output from the pressure detection unit, the pulse waves being pressure components superimposed on the pressurizing pressure in synchronization with the body's pulse; a blood flow sound detection unit configured to detect blood flow sounds that occur during a period of changing the pressurizing pressure; a pulse wave envelope data generation unit configured to generate data for a pulse wave envelope that associates amplitude values of the pulse waves detected by the pulse wave detection unit with pressurizing pressures at times when the pulse waves were generated; a blood pressure determination unit configured to determine a measured blood pressure value using the data for the pulse wave envelope; a blood flow sound envelope data generation unit configured to generate data for a blood flow sound envelope that associates amplitude values of blood flow sound signals, which are signals output from the blood flow sound detection unit, with the pressurizing pressures at times when the blood flow sound signals were generated; a blood pressure variation determination unit configured to use the data for the pulse wave envelope and the data for the blood flow sound envelope to determine whether or not there is periodic variation in the blood pressure during the period of changing the pressurizing pressure; and a control unit configured to perform control according to the determination result of the blood pressure variation determination unit.

The blood pressure measurement method according to one or more embodiments of the claimed invention includes: a pulse wave detection step of detecting pulse waves in a pressure signal of a cuff attached at a measurement site of a body, the pressure signal being detected during a period of reducing a pressurizing pressure applied by the cuff to the measurement site, the pulse waves being pressure components superimposed on the pressurizing pressure in synchronization with the body's pulse; a blood flow sound acquiring step of acquiring blood flow sound signals corresponding to blood flow sounds that occur during a period of changing the pressurizing pressure; a pulse wave envelope data generation step of generating data for a pulse wave envelope that associates amplitude values of the pulse waves detected in the pulse wave detection step with the pressurizing pressures at times when the pulse waves were generated; a blood pressure determination step of determining a measured blood pressure value using the data for the pulse wave envelope; a blood flow sound envelope data generation step of generating data for a blood flow sound envelope that associates amplitude values of the blood flow sound signals acquired in the blood flow sound acquiring step with the pressurizing pressures at times when the blood flow sound signals were generated; a blood pressure variation determination step of using the data for the pulse wave envelope and the data for the blood flow sound envelope to determine whether or not there is periodic variation in the blood pressure during the period of changing the pressurizing pressure; and a control step of performing control according to the determination result of the blood pressure variation determination step.

A non-transitory computer readable medium having stored thereon a blood pressure measurement program according to one or more embodiments of the claimed invention, wherein the program causes a computer to execute the steps of the blood pressure measurement method.

According to one or more embodiments of the claimed invention, it is possible to provide a blood pressure measurement apparatus, a blood pressure measurement method, and a blood pressure measurement program, according to which it is possible to prevent a decrease in the blood pressure measurement accuracy caused by slight variations in the blood pressure, without increasing the accuracy of measuring the pressure in the cuff.

BRIEF DESCRIPTION OF DRAWINGS

FIG. 6 is a diagram showing a result of simulating change in the shape of a pulse wave envelope in a case where there is respiratory variation.

FIG. 7 is a diagram showing a result of simulating change in the shape of a pulse wave envelope in a case where there is respiratory variation.

DETAILED DESCRIPTION OF INVENTION

Hereinafter, an embodiment of the claimed invention will be described with reference to the drawings.

Figure 1:
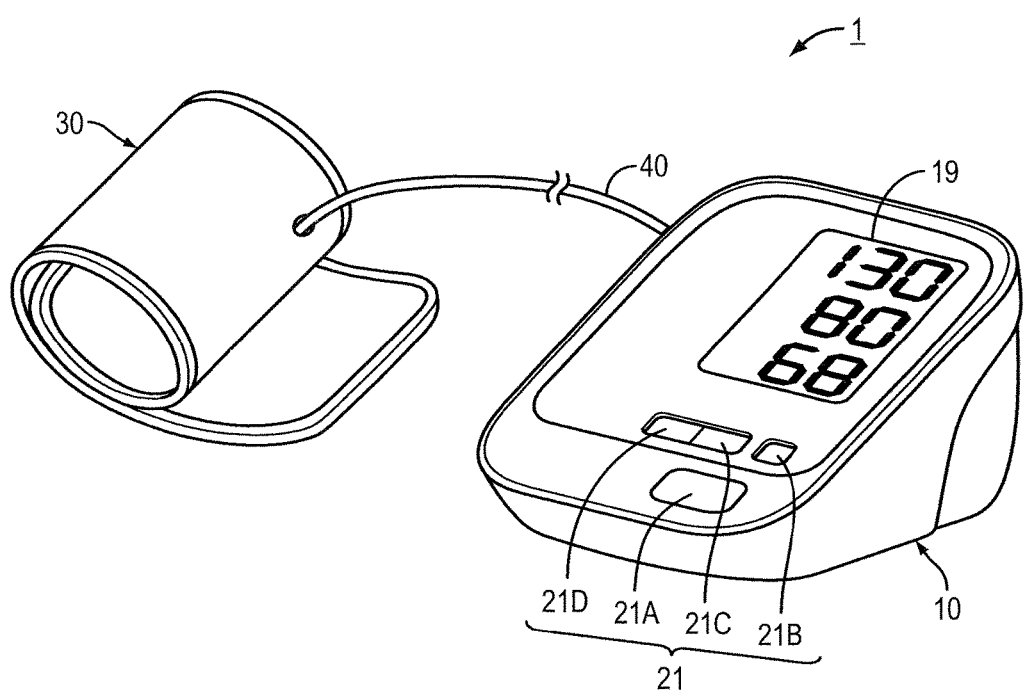
FIG. 1 is an external appearance diagram showing an overall configuration of a blood pressure measurement apparatus for describing an embodiment of the claimed invention.

FIG. 1 is an external appearance diagram showing an overall configuration of a blood pressure measurement apparatus for describing an embodiment of the claimed invention.

A blood pressure measurement apparatus 1 includes a main body portion 10, a cuff 30 that can be wrapped around an upper arm of a measurement subject, and an air tube 40 that connects the main body portion 10 and the cuff 30. The cuff 30 includes an air bladder 31 (see FIG. 2), and the air tube 40 is connected to the air bladder 31.

With respect to one or more embodiments of the claimed invention, "cuff" refers to a band-shaped or tube-shaped structure that has an inner cavity and can be wrapped around a measurement site (e.g., an upper arm, a wrist, etc.) of a body. Also, "cuff" refers to an object that is used for blood pressure measurement by pressurizing an artery of a measurement subject with insertion of a fluid such as air or a liquid into an inner cavity.

"Cuff" indicates a concept including a fluid bladder and a wrapping means for wrapping the fluid bladder around a body, and is called an armband in some cases. In the example shown in FIG. 1, the cuff 30 and the main body portion 10 are separate, but the cuff 30 may be integrated with the main body portion 10.

The main body portion 10 includes a display unit 19 that is constituted by, for example, liquid crystal, or the like for displaying various types of information, such as a blood pressure value and a pulse count, and an operation unit 21 that includes multiple switches 21A, 21B, 21C, and 21D for receiving instructions from a user (measurement subject).

The operation unit 21 includes a measure/stop switch 21A that receives input of instructions for switching on or off a power supply and instructions to start and end measurement, a memory switch 21B for receiving an instruction to read out information such as blood pressure data stored in the main body portion 10 and display it on the display unit 19, and arrow switches 21C and 21D for receiving instructions to increment/decrement the memory number when calling information.

Figure 2:
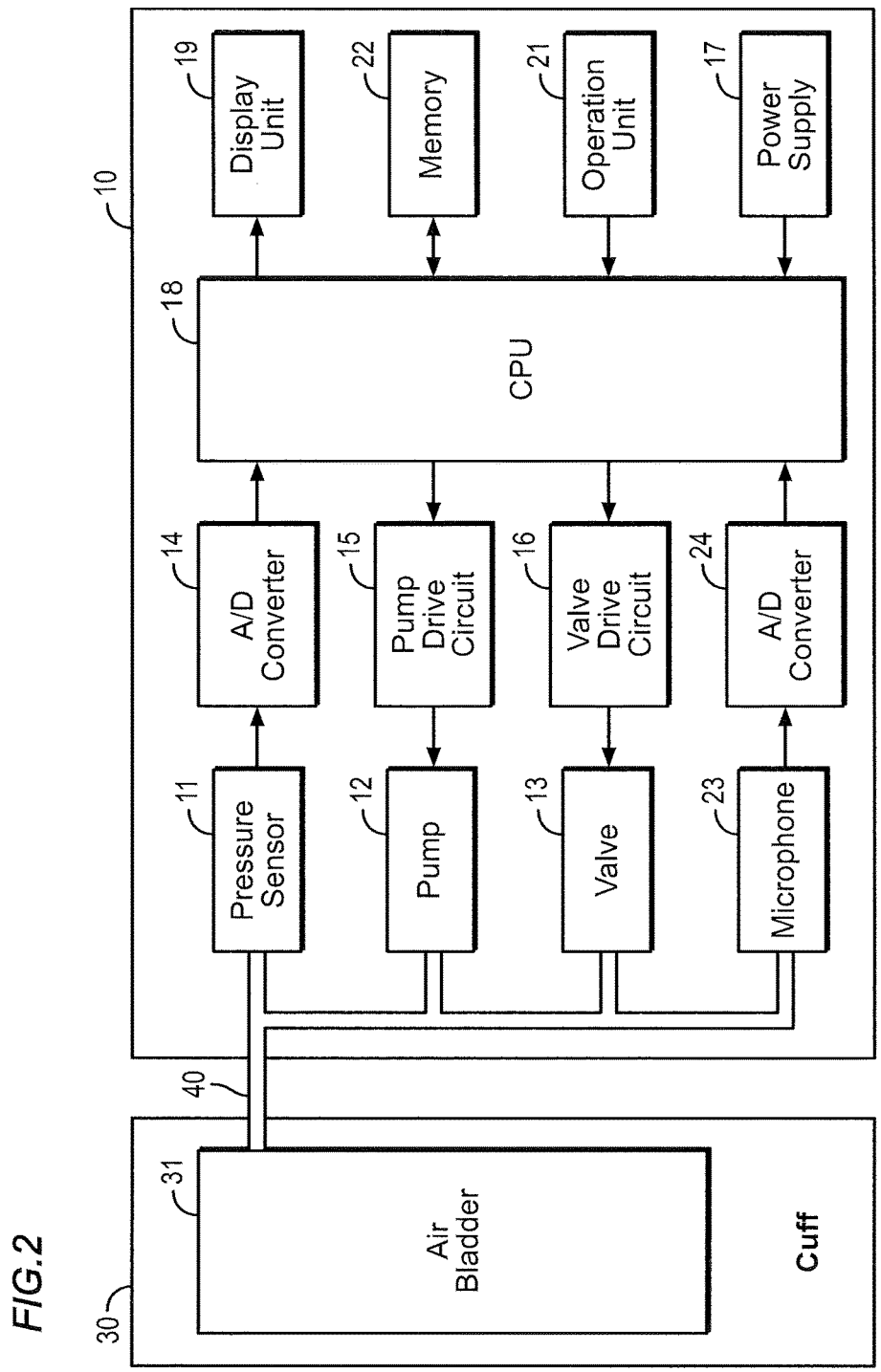
FIG. 2 is a diagram showing an internal configuration of a main body portion 10 in a blood pressure measurement apparatus 1 shown in FIG. 1.

FIG. 2 is a diagram showing an internal configuration of a main body portion 10 in the blood pressure measurement apparatus 1 shown in FIG. 1.

The main body portion 10 includes a pressure sensor 11, a pump 12, and an exhaust valve (referred to below as "valve") 13, which are connected to the air tube 40, a microphone 23, an A/D converter 14, a pump drive circuit 15, a valve drive circuit 16, an A/D converter 24, a power supply 17 that supplies electrical power to the units of the main body 10, the display unit 19, a control unit (CPU) 18 that performs overall control of the main body portion 10 and performs calculation processing, the operation unit 21, and the memory 22.

The pump 12 supplies air to the air bladder 31 in order to increase the pressurizing pressure applied by the cuff 30 to the measurement area (referred to below as "cuff pressure" as well).

The valve 13 is opened/closed in order to discharge air from or seal air in the air bladder 31.

The pump drive circuit 15 controls the driving of the pump 12 based on a control signal obtained from the CPU 18.

The valve drive circuit 16 controls the opening and closing of the valve 13 based on a control signal obtained from the CPU 18.

A pressurizing pressure adjustment unit that changes the pressurizing pressure applied by the cuff 30 to the measurement site (cuff pressure) is constituted by the pump 12, the valve 13, the pump drive circuit 15, and the valve drive circuit 16.

The pressure sensor 11 is a sensor that detects the pressure in the cuff 30 (air pressure in the air bladder 31) and outputs an electrical signal (cuff pressure signal).

The A/D converter 14 converts the analog cuff pressure signal output from the pressure sensor 11 into a digital signal and outputs it to the CPU 18.

The microphone 23 detects Korotkoff sounds (hereinafter to be referred to as "K sounds"), which are blood flow sounds (vascular sounds) of a measurement subject and outputs electrical signals (K sound signals).

The A/D converter 24 converts the analog K sound signals output from the microphone 23 into digital signals and outputs them to the CPU 18.

The memory 22 includes a read-only memory (ROM) that stores programs, data, and so on for causing the CPU 18 to perform predetermined operations, a random access memory (RAM) used as a working memory, and a flash memory that holds measured blood pressure data and the like.

Figure 3:
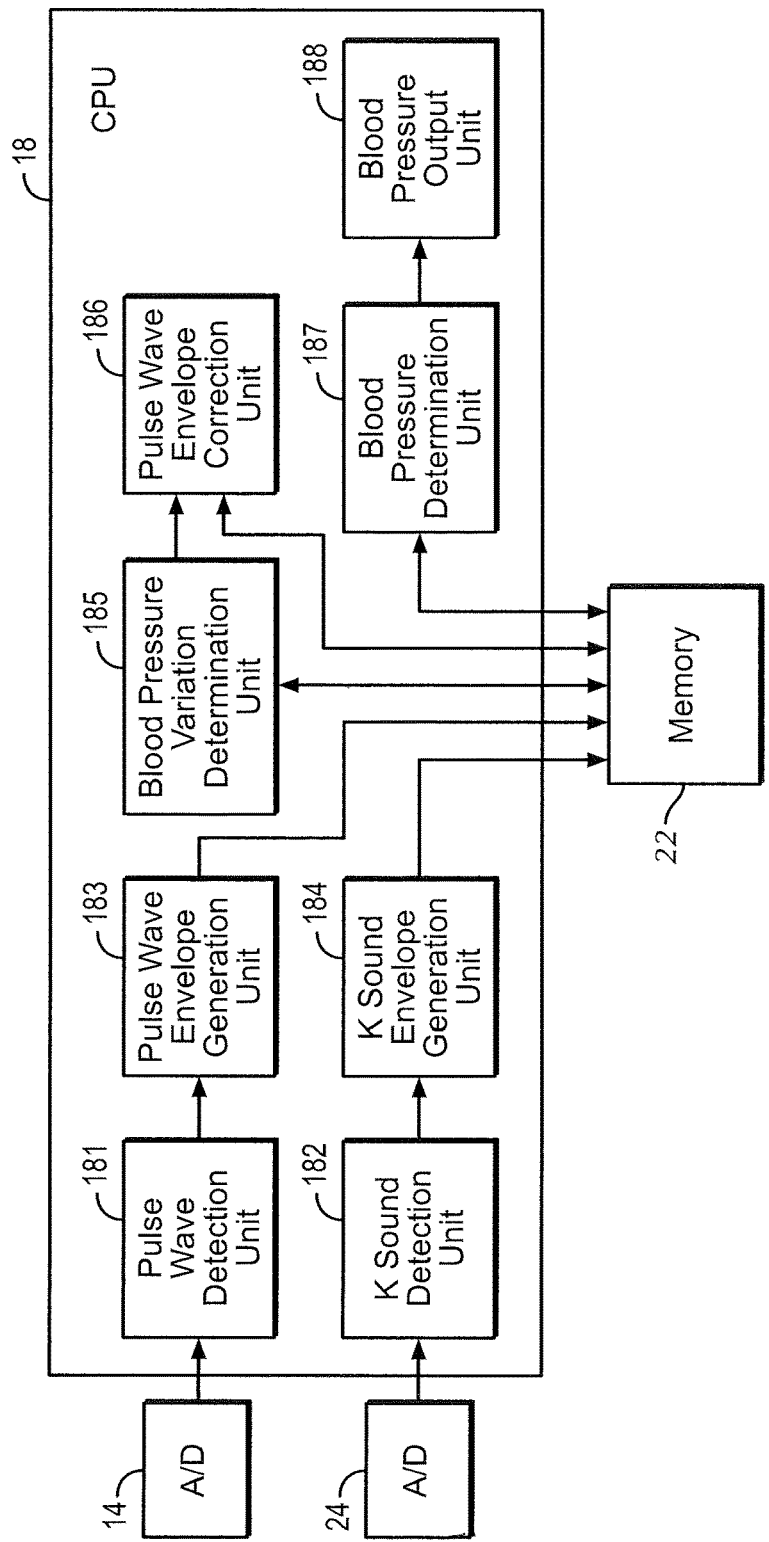
FIG. 3 is a diagram of functional blocks realized by a CPU 18 shown in FIG. 2 reading out a program stored in a ROM and executing it.

FIG. 3 is a diagram of functional blocks realized by the CPU 18 shown in FIG. 2 reading out a blood pressure measurement program stored in the ROM and executing it.

The CPU 18 includes a pulse wave detection unit 181, a K sound detection unit 182, a pulse wave envelope generation unit 183, a K sound envelope generation unit 184, a blood pressure variation determination unit 185, a pulse wave envelope correction unit 186, a blood pressure determination unit 187, and a blood pressure output unit 188.

These are functions realized in the CPU 18 mainly by the CPU 18 reading out programs stored in the memory 22 and executing them, but a portion or all of these functions may be realized using a hardware configuration.

In the cuff pressure signal input from the A/D converter 14, the pulse wave detection unit 181 detects the cuff pressure and pulse waves, which are pressure components that are superimposed on the cuff pressure, using filter processing, for example. The pulse wave detection unit 181 uses the digital signal from the A/D converter 14 representing the cuff pressure signal in the cuff 30 as produced by the pressure sensor 11. The pulse wave detection unit 181 filters the digital signal from the A/D converter to extract signals representing the pulse waves.

The pulse wave envelope generation unit 183 calculates the amplitude values of the pulse waves detected by the pulse wave detection unit 181 and stores the calculated amplitude values and the cuff pressures at the times when the pulse waves were generated in the memory 22 in association with each other. A line connecting the amplitude values in the case where the cuff pressures recorded in the memory 22 and the amplitude values of the corresponding pulse waves are expressed in a graph is referred to as a pulse wave envelope.

The K sound detection unit 182 detects the K sound signals and their levels (which correspond to the amplitudes) by acquiring the K sound signals from the A/D converter 24. The K sound detection unit 182 uses the digital signal from the A/D converter 24 representing the K sound signals as produced by the microphone 23. The K sound detection unit 182 detects the K sound signals and detects the amplitudes of the K sound signals.

The K sound envelope generation unit 184 stores the amplitudes of the K sound signals and the cuff pressures at the times when the K sound signals were generated, in the memory 22 in association with each other. The K sound envelope generation unit 184 acquires information regarding the cuff pressure from the pulse wave detection unit 181. A line connecting amplitude values in the case where the cuff pressures recorded in the memory 22 and the amplitude values of the corresponding K sound signals are expressed in a graph is referred to as a K sound envelope.

The blood pressure variation determination unit 185 uses the data included in the pulse wave envelope and the data included in the K sound envelope to detect whether or not there is variation (mainly respiratory variation) in the blood pressure during blood pressure measurement, and the determination result is stored in the memory 22.

Specifically, the blood pressure variation determination unit 185 determines the shapes of the pulse wave envelope and of the K sound envelope and determines based on the determination result whether or not there was variation in the blood pressure during blood pressure measurement. Hereinafter, the reason why it is possible to determine whether or not there was blood pressure variation based on the shapes of the pulse wave envelope and of the K sound envelope will be described.

FIGS. 4 to 9 show results of simulating change in the shape of the pulse wave envelope in cases where there is respiratory variation.

Figure 4:
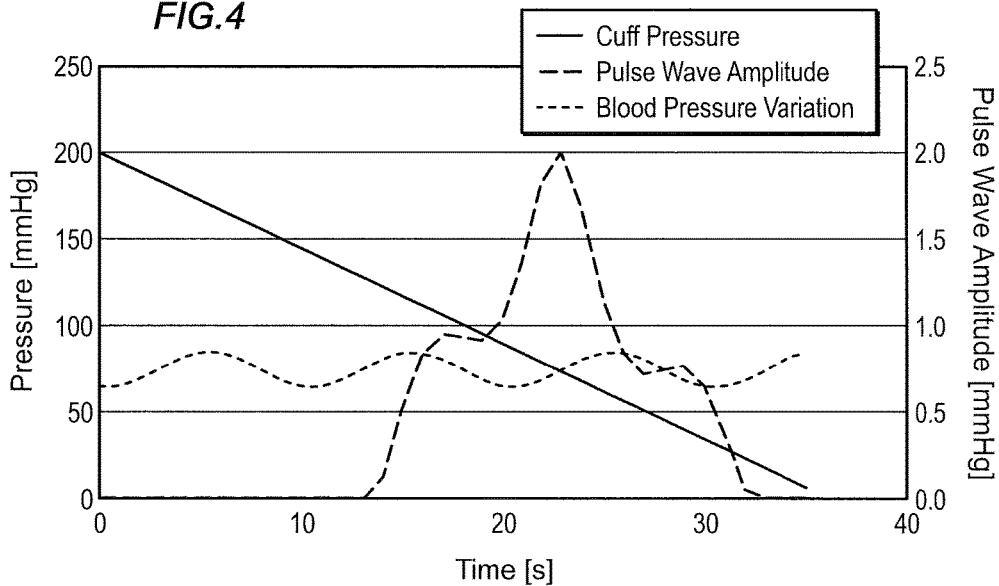
FIG. 4 is a diagram showing a result of simulating change in the shape of a pulse wave envelope in a case where there is respiratory variation.
Figure 8:
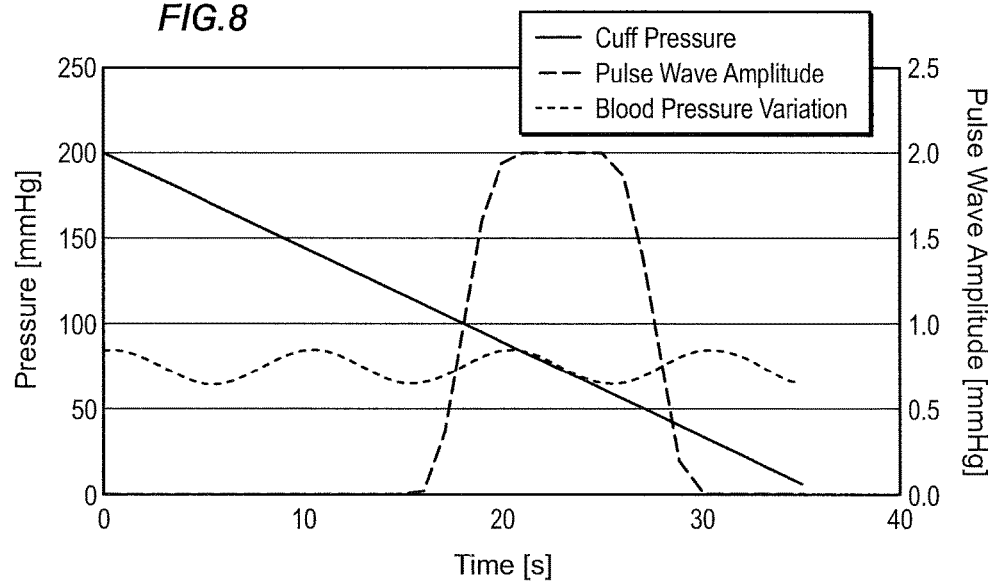
FIG. 8 is a diagram showing a result of simulating change in the shape of a pulse wave envelope in a case where there is respiratory variation.

FIGS. 4, 6, and 8 show waveforms of the cuff pressure and the blood pressure variation (period: 10 seconds, variation width: 10 mmHg) on which the simulations are premised.

Also, FIGS. 4, 6, and 8 also show the waveforms of the pulse wave amplitudes detected in the process of reducing the cuff pressure.

Figure 5:
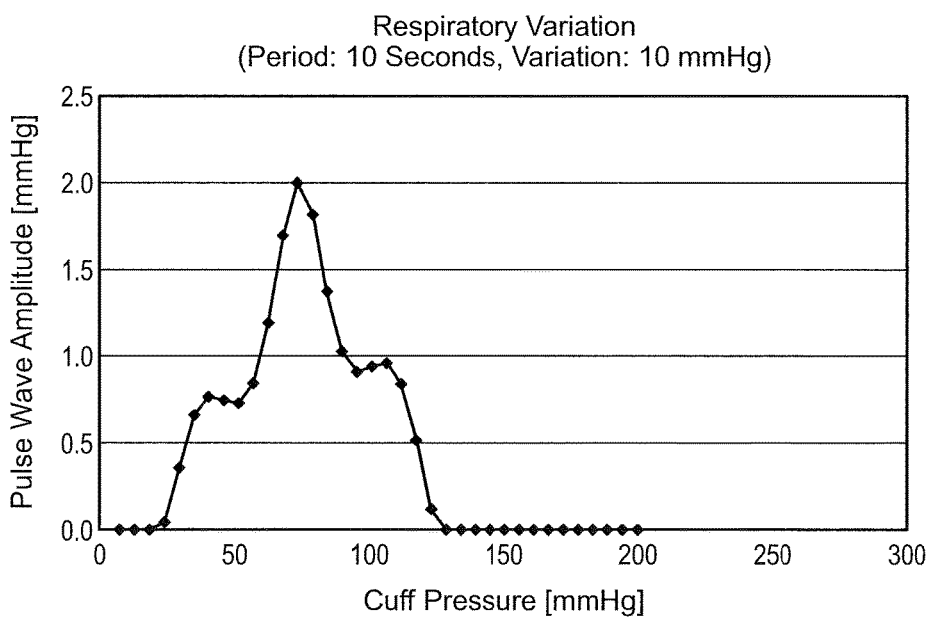
FIG. 5 is a diagram showing a result of simulating change in the shape of a pulse wave envelope in a case where there is respiratory variation.
Figure 9:
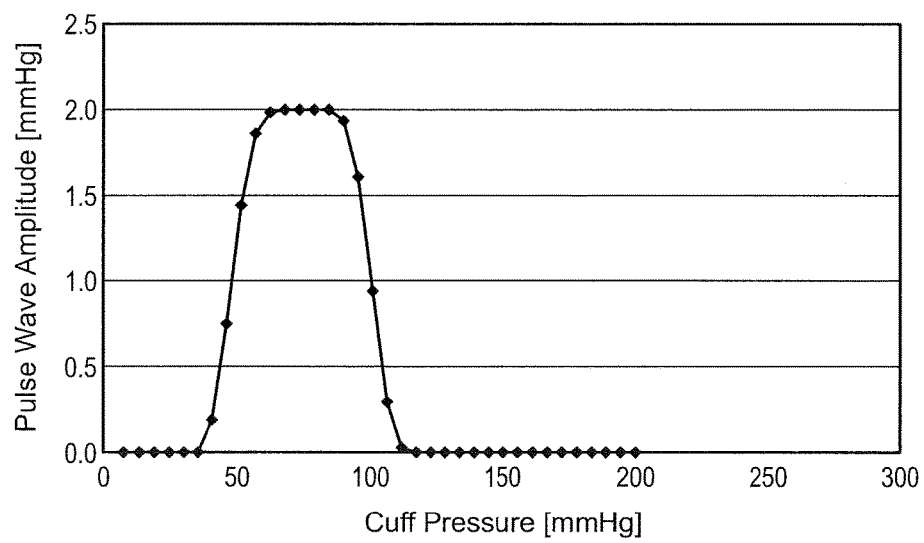
FIG. 9 is a diagram showing a result of simulating change in the shape of a pulse wave envelope in a case where there is respiratory variation.

FIGS. 5, 7, and 9 show the waveforms of the pulse wave amplitudes shown in FIGS. 4, 6, and 8, with the cuff pressure indicated on the horizontal axis.

As shown in FIGS. 5, 7, and 9, if there is blood pressure variation, the shape of the pulse wave envelope will be a shape with multiple peak portions as in FIGS. 5 and 7, or a trapezoidal shape as in FIG. 9, which rises accompanying an increase in the cuff pressure, subsequently becomes flat, and falls thereafter.

In the present specification, a peak portion of an envelope refers to an amplitude value corresponding to the cuff pressure at a timing at which the amplitude value changes from increasing to decreasing. Also, if there are multiple peak portions in the envelope, the amplitude value with the smallest value among the amplitude values between adjacent peak portions, and the amplitude values of the two ends of the envelope are referred to as "trough portions". Note that among peak portions that correspond to the foregoing definition, a peak portion whose amplitude value differs from the amplitude values of both adjacent trough portions by less than a threshold value is not treated as a peak portion.

The blood pressure variation determination unit 185 detects peak portions in the pulse wave envelope so as to determine whether or not the envelope has a shape with multiple peak portions.

As described above, among the detected peak portions, the blood pressure variation determination unit 185 does not count a peak portion whose amplitude value differs from the amplitude values of both adjacent trough portions by less than a threshold value as peak portions included in the pulse wave envelope.

Also, the blood pressure variation determination unit 185 calculates the displacement amounts of amplitude values of two pulse waves whose detection times are adjacent, and if the cuff pressure at which the displacement amounts thereof are less than a threshold value TH2 is continued for a predetermined amount of time or more, it is determined that the shape of the pulse wave envelope is a trapezoidal shape.

For the threshold value TH1, the threshold value TH2, and the predetermined number, it is sufficient that the data for many pulse wave envelopes when blood pressure variation has occurred and when blood pressure variation has not occurred is analyzed so as to determine a value according to which erroneous determination does not occur in the subsequent blood pressure variation determination.

Even if there is no blood pressure variation, there is a possibility that the pulse wave envelope will have a shape such as those shown in FIGS. 5, 7, and 9, and therefore it is not possible to determine whether or not there is blood pressure variation using only the shape of the pulse wave envelope.

FIG. 10 shows diagrams showing results of inducing respiratory variation under controlled respiration and verifying the change in the pulse wave amplitude and the K sound amplitude at a fixed cuff pressure. Since the cuff pressure is constant, the variation in the pulse wave amplitude in the verification result largely matches the respiratory variation in the blood pressure.

Figure 10A:
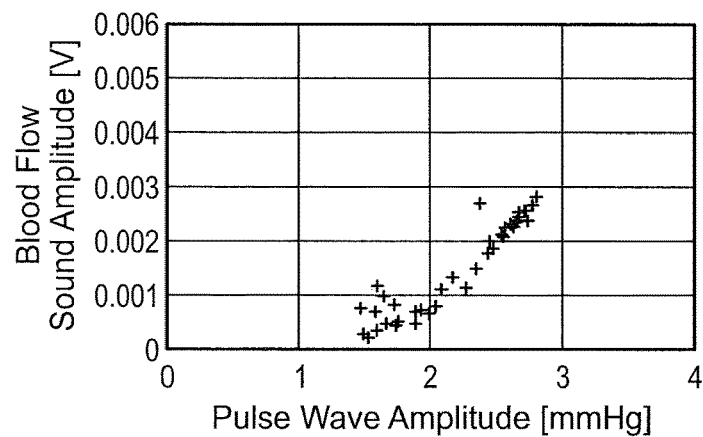
FIGS. 10A-10C show diagrams showing results of inducing respiratory variation under controlled respiration and verifying the change in the pulse wave amplitude and a K sound amplitude on the basis of a fixed cuff pressure.
Figure 10B:
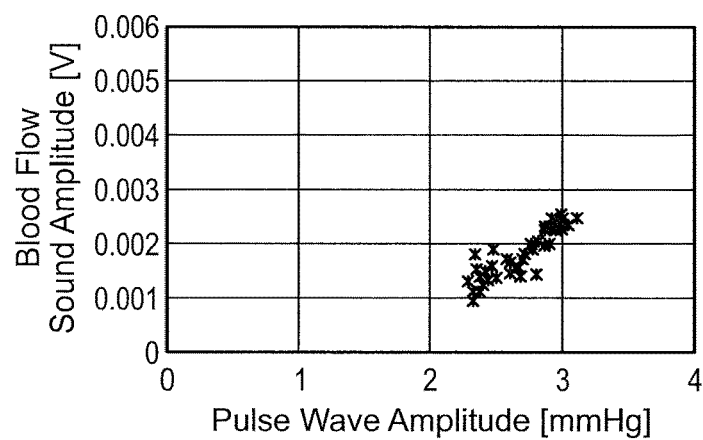
Figure 10C:
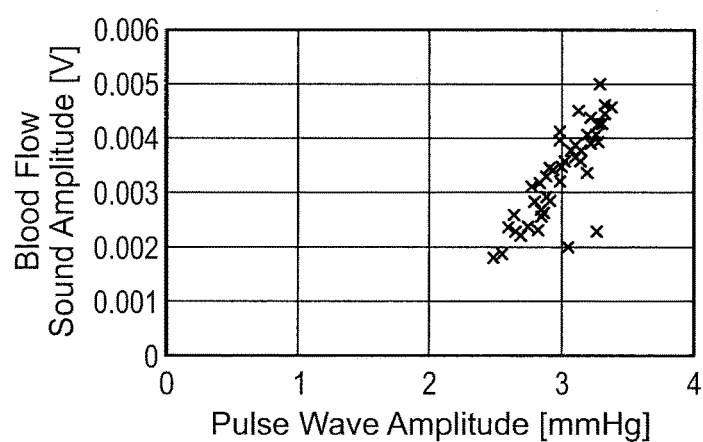

FIG. 10A shows the results of verification when the respiration period is 6 seconds, FIG. 10B shows the results of verification when the respiration period is 10 seconds, and FIG. 10C shows the results of verification when the respiration period is 20 seconds.

Based on the results shown in FIG. 10, it can be understood that the K sound amplitude and the pulse wave amplitude are positively correlated. Accordingly, if there is blood pressure variation, it is thought that some kind of change will appear in the shape of the K sound envelope as well.

Figure 11:
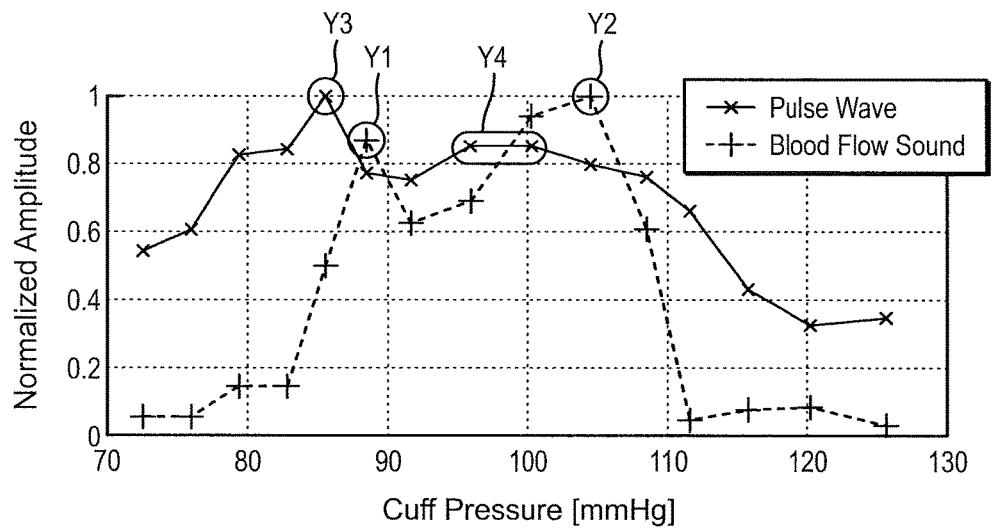
FIG. 11 is a diagram showing a result of obtaining the pulse wave envelope and the K sound envelope in a case where respiratory variation has occurred.
Figure 12:
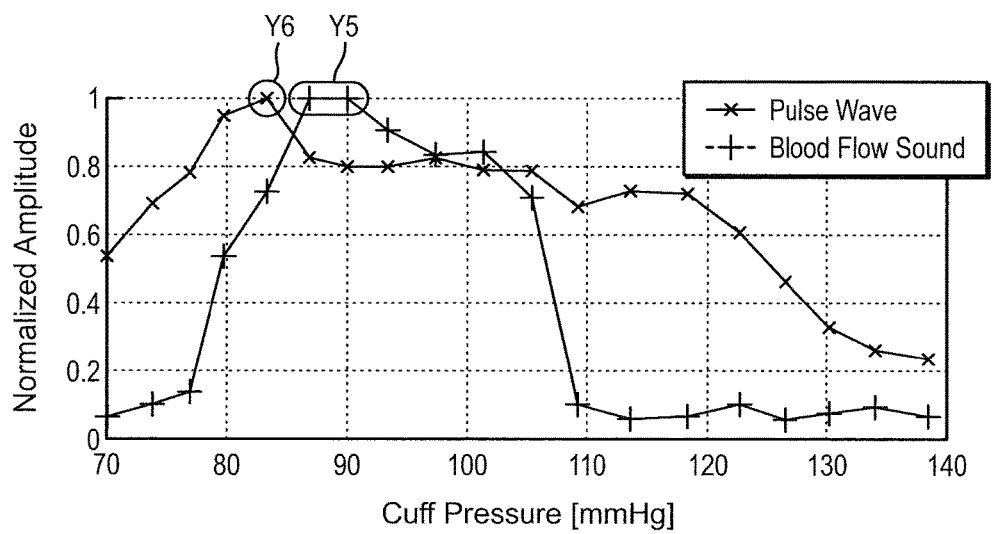
FIG. 12 is a diagram showing a result of obtaining the pulse wave envelope and the K sound envelope in a case where respiratory variation has not occurred.

FIG. 11 is a diagram showing a result of obtaining the pulse wave envelope and the K sound envelope in the case where respiratory variation has occurred. FIG. 12 is a diagram showing a result of obtaining the pulse wave envelope and the K sound envelope in the case where respiratory variation has not occurred. In FIGS. 11 and 12, the vertical axis indicates amplitude values obtained by normalizing the maximum value at 1.

The K sound envelope shown in FIG. 11 has peak portions Y1 and Y2, and the pulse wave envelope has peak portions Y3 and Y4. On the other hand, the K sound envelope shown in FIG. 12 has a peak portion Y5, and the pulse wave envelope has a peak portion Y6. Other than what is shown in FIGS. 11 and 12, many measurement subjects are subjected to verification, and as a result, it is understood that when blood pressure variation has occurred, the K sound envelope also has a shape with multiple peak portions.

In view of this, the blood pressure variation determination unit 185 detects peak portions in the K sound envelope so as to determine whether or not the K sound envelope has a shape with multiple peak portions.

As described above, among the detected peak portions, the blood pressure variation determination unit 185 does not count a peak portion whose amplitude value differs from the amplitude values of both adjacent trough portions by less than a threshold value TH3 as peak portions included in the K sound envelope.

For the threshold value TH3, it is sufficient that data for many K sound envelopes in the case where blood pressure variation has occurred and in the case where blood pressure variation has not occurred are analyzed so as to determine a value according to which erroneous determination does not occur in the blood pressure variation determination.

Also, if it is determined according to the foregoing method that the pulse wave envelope has a shape with multiple peak portions or has a trapezoidal shape and the K sound envelope has a shape with multiple peak portions, the blood pressure variation determination unit 185 determines that there is blood pressure variation.

Returning to the description of FIG. 3, if it is determined by the blood pressure variation determination unit 185 that there is blood pressure variation, the pulse wave envelope correction unit 186 corrects the shape of the pulse wave envelope.

Figure 13A:
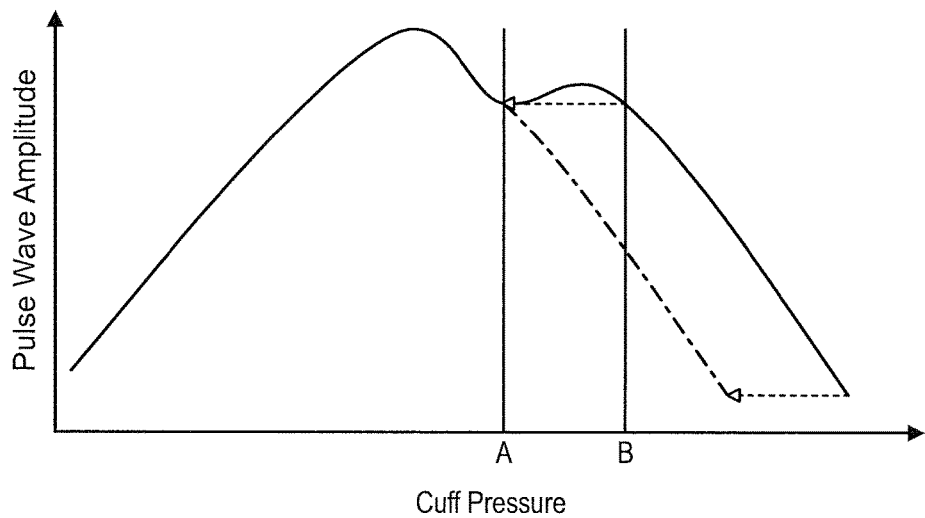
FIGS. 13A-13B are diagrams for illustrating a method of correcting a pulse wave envelope using a pulse wave envelope correction unit 186.
Figure 13B:
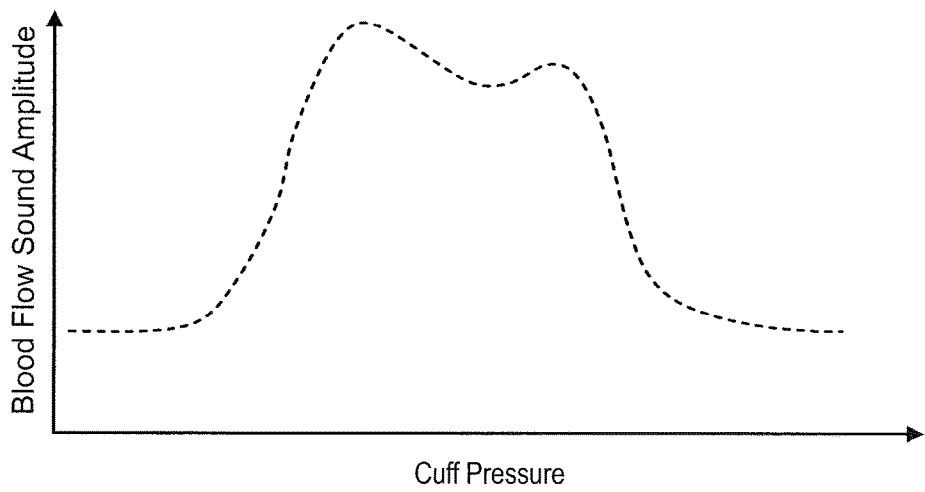
Figure 14A:
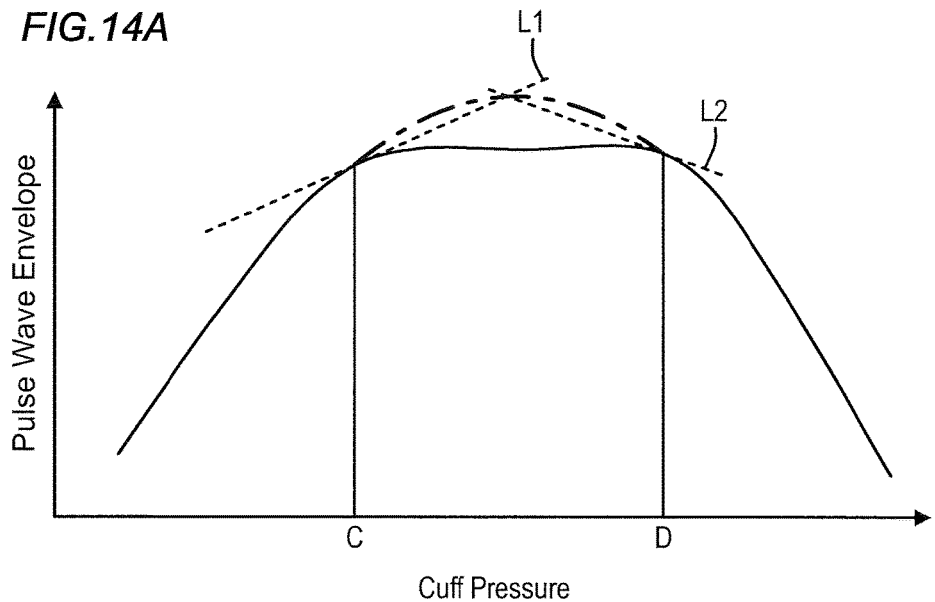
FIGS. 14A-14B are diagrams for illustrating a method of correcting a pulse wave envelope using the pulse wave envelope correction unit 186.
Figure 14B:
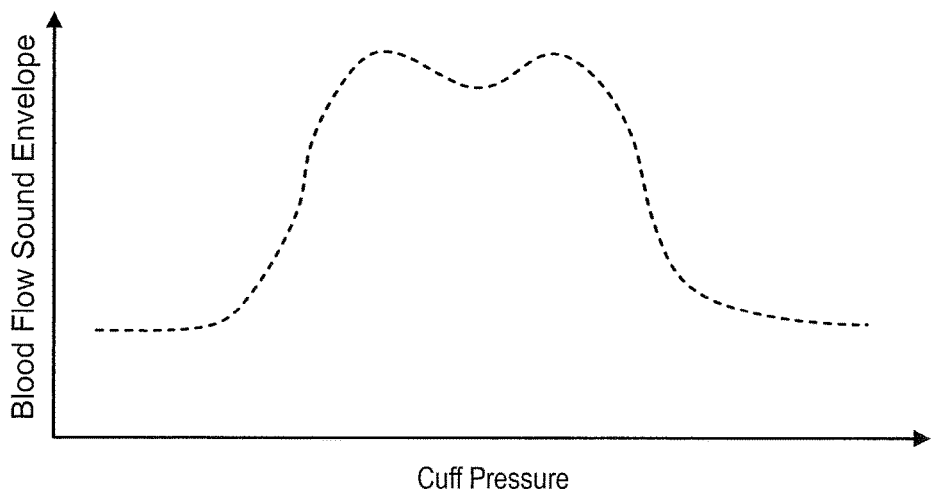

FIGS. 13 and 14 are diagrams for describing a method for correcting a pulse wave envelope according to the pulse wave envelope correction unit 186.

When a K sound envelope having two peak portions is obtained as shown in FIG. 13B and a pulse wave envelope having two peak portions is obtained as shown in FIG. 13A, it is determined that there was blood pressure variation.

In this case, the pulse wave envelope correction unit 186 selects the higher of the two peak portions (the peak portion with the greater amplitude) in the pulse wave envelope. Then, the selected peak portion and the envelope extending to the cuff pressure corresponding to the adjacent trough portion (reference numeral A in FIG. 13A) are retained, and a new envelope is interpolated by deleting the envelope corresponding to the cuff pressures that exceed cuff pressure A.

For example, among amplitude values corresponding to cuff pressures greater than cuff pressure A, the pulse wave envelope correction unit 186 selects those with the same amplitude value as the amplitude value corresponding to cuff pressure A. Then, the portion of the envelope that is greater than or equal to the cuff pressure corresponding to the selected amplitude value (reference numeral B in FIG. 13A) is shifted to the low-pressure side by a pressure determined using (cuff pressure B—cuff pressure A). The thus-interpolated envelope is indicated in FIG. 13A by a one-dot chain line.

Also, if there is blood pressure variation and the pulse wave envelope has a trapezoidal shape as shown in FIG. 14, the pulse wave envelope correction unit 186 deletes the flat portion of the pulse wave envelope and interpolates the amplitude values for the cuff pressures corresponding to the flat portion.

For example, the pulse wave envelope correction unit 186 determines the cuff pressure in the case where the change in the size of the amplitude value is less than a threshold value TH2 (reference numeral C in FIG. 14A) and the cuff pressure in the case where the change in the size of the amplitude value returns to being greater than or equal to the threshold value TH2 (reference numeral D in FIG. 14A).

Then, the pulse wave envelope correction unit 186 sets a line L1 that passes through the amplitude value corresponding to the cuff pressure C and does not intersect the pulse wave amplitude envelope, and a line L2 that passes through the amplitude value corresponding to the cuff pressure D and does not intersect the pulse wave amplitude envelope.

The pulse wave envelope correction unit 186 interpolates a curved line that connects the point at which the line L1 and the line L2 intersect, the amplitude value corresponding to the cuff pressure C, and the amplitude value corresponding to the cuff pressure D (single-dot chain line in FIG. 14A).

It is sufficient that the curved line is generated so that the envelope corresponding to the cuff pressures that are less than or equal to the cuff pressure C and the slope of the envelope corresponding to the cuff pressures that are less than or equal to the cuff pressure D connect smoothly.

Figure 15:
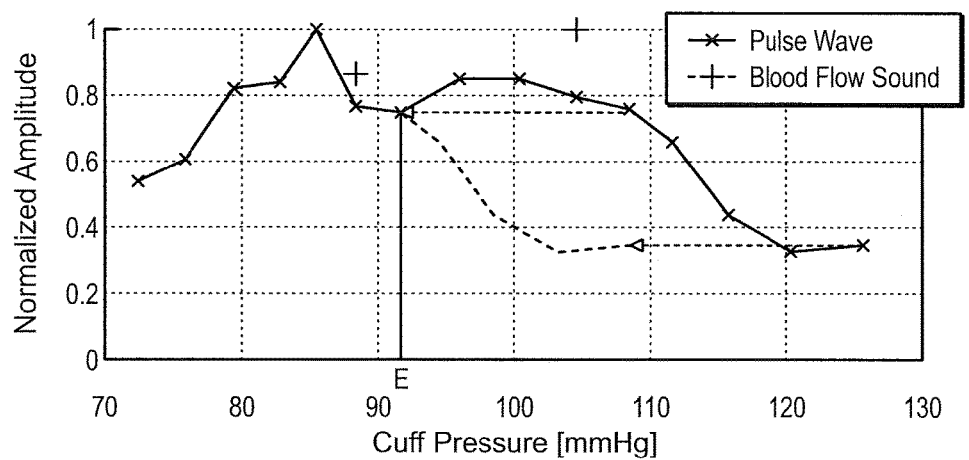
FIG. 15 is a diagram for illustrating pulse wave envelope correction processing for the data shown in FIG. 11.

FIG. 15 is a diagram for describing pulse wave envelope correction processing performed with respect to the data shown in FIG. 11. As shown in FIG. 15, the pulse wave envelope correction unit 186 deletes the portions of the pulse wave envelope that exceed the cuff pressure E and generates the broken line portion by interpolation.

Figure 16:
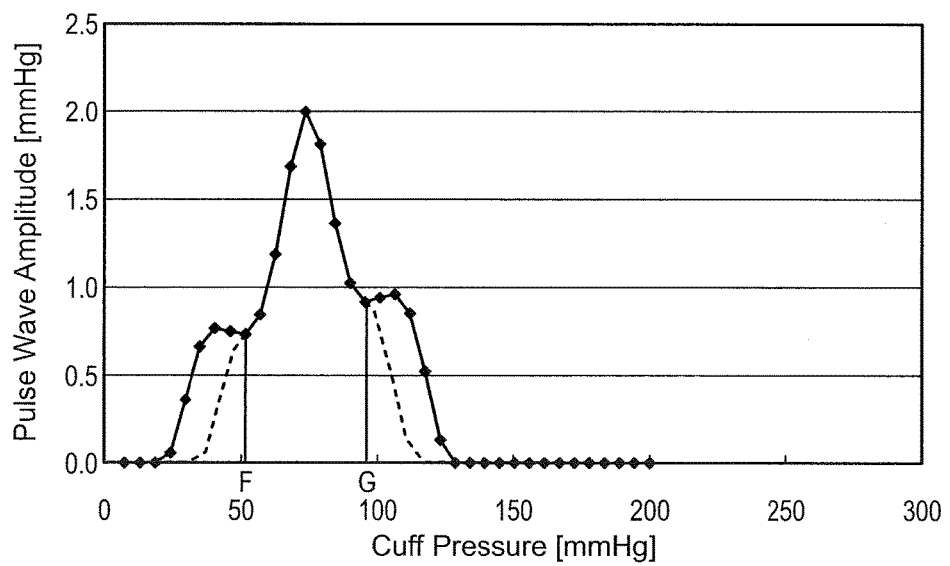
FIG. 16 is a diagram for illustrating pulse wave envelope correction processing for the data shown in FIG. 5.

FIG. 16 is a diagram for describing pulse wave envelope correction processing performed with respect to the data shown in FIG. 5. As shown in FIG. 16, the pulse wave envelope correction unit 186 deletes the portions of the pulse wave envelope that are less than or equal to the cuff pressure F and portions that are greater than or equal to the cuff pressure G and generates the broken line portions by interpolation.

Returning to the description of FIG. 3, the blood pressure determination unit 187 uses the data for the pulse wave envelope stored in the memory 22 to determine the measured blood pressure value. The blood pressure determination unit 187 uses the corrected pulse wave envelope (step S8) or non-corrected pulse wave envelope (step S11), as will be described later, to determine the measured blood pressure value. The blood pressure determination unit 187 determines the measured blood pressure value such that, based on the envelope, which is either one of the corrected pulse wave envelope or non-corrected pulse wave envelope, (i) the cuff pressure at the time of generation of the pulse wave with the greatest amplitude is set as the average blood pressure value, (ii) then, among the cuff pressures that are greater than the average blood pressure value, a cuff pressure at the time of generation of a pulse wave with an amplitude that is the closest in value to a first predetermined percentage of the maximum value is set as the systolic blood pressure value, and (iii) among cuff pressures that are lower than the average blood pressure value, a cuff pressure at the time of generation of a pulse wave with an amplitude that is closest in value to a second predetermined percentage of the maximum value is set as the diastolic blood pressure value.

The blood pressure output unit 188 outputs the information regarding the measured blood pressure value determined by the blood pressure determination unit 187 to the display unit 19 and causes the display unit 19 to display it. The blood pressure output unit 188 may output the information regarding the measured blood pressure value using a speaker or the like.

Figure 17:
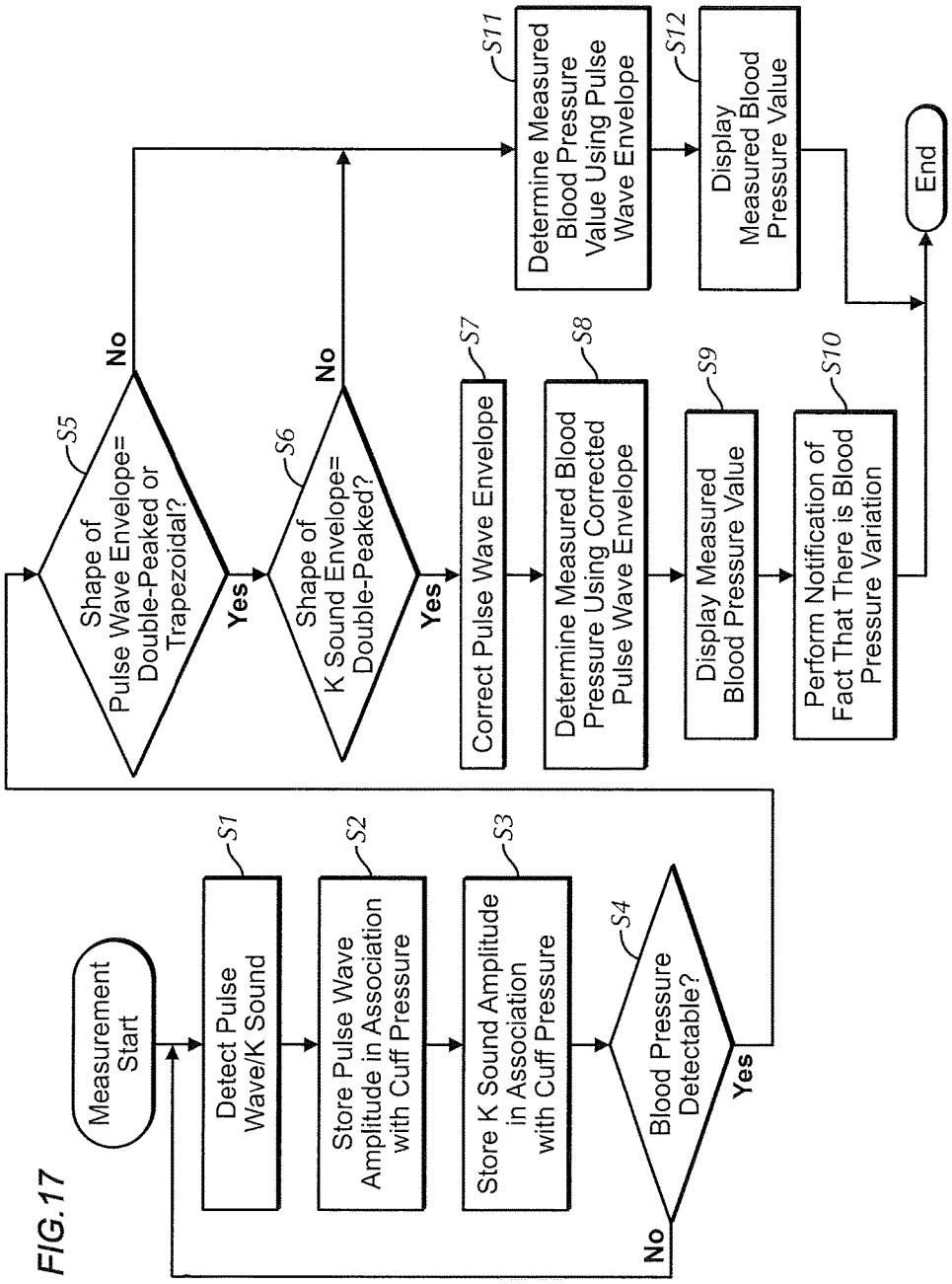
FIG. 17 is a flowchart for illustrating operations of the blood pressure measurement apparatus 1 shown in FIG. 1.

FIG. 17 is a flowchart for describing operations of the blood pressure measurement apparatus 1 shown in FIG. 1.

When the measure/stop switch 21A is pressed so as to instruct the start of blood pressure measurement, the CPU 18 closes the valve 13 and starts to increase the pressurizing pressure applied by the cuff 30 to the arm (application of pressure to the arm) by inserting air into the cuff 30 using the pump 12.

When the cuff pressure reaches a target value that is sufficiently greater than the systolic blood pressure value, the CPU 18 stops the pump 12 and controls the valve 13 so as to start reduction of the cuff pressure.

During the period of reducing the cuff pressure, the CPU 18 detects the pulse waves and the cuff pressure in the cuff pressure signal, which is the output of the pressure sensor 11, and acquires K sound signals, which are the output of the microphone 23 (step S1).

The CPU 18 calculates the amplitude values of the detected pulse waves and stores the calculated amplitude values and the cuff pressures at the times when the pulse waves were generated in the memory 22 in association with each other (step S2).

Also, the CPU 18 stores the amplitude values of the K sound signals acquired from the microphone 23 in the memory 22 in association with the cuff pressures at the times when the K sound signals were generated (step S3).

If a number of pulse wave amplitudes that is sufficient to determine the measured blood pressure value have been stored in the memory 22 (step S4: YES), the CPU 18 performs the processing of step S5, and if a number of pulse wave amplitudes that is sufficient to determine the measured blood pressure value have not been stored in the memory 22 (step S4: NO), the CPU 18 returns to the processing of step S1.

In step S5, the CPU 18 determines whether or not the pulse wave envelope based on the data stored in the memory 22 is a double-peak shape having multiple peaks or a trapezoidal shape.

If the pulse wave envelope is a double-peak shape or a trapezoidal shape (step S5: YES), the CPU 18 determines whether or not the K sound envelope based on the data stored in the memory 22 is a double-peak shape with multiple peak portions (step S6).

On the other hand, if the pulse wave envelope is not a double-peak shape or a trapezoidal shape (step S5: NO), the CPU 18 determines that blood pressure variation has not occurred, uses the data for the pulse wave envelope to determine the measured blood pressure value (step S11), and causes the display unit 19 to display the measured blood pressure value that was determined (step S12).

If the result of the determination in step S6 is YES, the CPU 18 determines that blood pressure variation has occurred and performs the processing of step S7, and if the result of the determination in step S6 is NO, the CPU 18 determines that blood pressure variation has not occurred and performs the processing of step S11.

In step S7, the CPU 18 corrects the pulse wave envelope in accordance with the shape of the pulse wave envelope.

Then, the CPU 18 uses the data for the corrected pulse wave envelope to determine the measured blood pressure value (step S8), and causes the display unit 19 to display the measured blood pressure value that was determined (step S9). Also, the CPU 18 causes the display unit 19 to display information indicating the fact that blood pressure variation occurred in blood pressure measurement as well (step S10).

As described above, the blood pressure measurement apparatus 1 of the present embodiment determines whether or not there is blood pressure variation during measurement according to the shapes of the pulse wave envelope and the K sound envelope, and if it is determined that there is blood pressure variation, the blood pressure measurement apparatus 1 corrects the shape of the pulse wave envelope and thereafter determines the measured blood pressure value. For this reason, it is possible to accurately determine whether or not there is blood pressure variation, and even if there is blood pressure variation, it is possible to prevent the blood pressure measurement accuracy from decreasing.

Also, according to the blood pressure measurement apparatus 1, if there is blood pressure variation, it is possible to perform notification of the measured blood pressure value as well as the fact that there was blood pressure variation. For this reason, upon viewing the information indicating the fact that there was blood pressure variation, the measurement subject can redo blood pressure measurement and user-friendliness can be improved.

Note that here, it has been described that the measured blood pressure value is obtained by correcting the pulse wave envelope if there is blood pressure variation, but if there is blood pressure variation, it is possible to cause the display unit 19 to display only information indicating that there was blood pressure variation and stop blood pressure measurement.

The functions realized by the CPU 18 of the blood pressure measurement apparatus 1 can also be realized by a general-use computer.

For example, a configuration is possible in which a unit including a configuration not including the CPU 18, the display unit 19, the operation unit 21, and the memory 22 shown in FIG. 2 is used by being externally connected to a computer in which a display unit, an operation unit, and a memory are connected.

In this configuration, the unit can be controlled from the computer, and using a signal sent from the unit, the computer performs the processing of steps S1 to S12 shown in FIG. 16, and it is thereby possible to realize functions similar to those of the blood pressure measurement apparatus 1 of the present embodiment.

Also, the blood pressure measurement method performed by the CPU 18 of the present embodiment can be provided as a program. This kind of program is stored in a computer-readable non-transitory storage medium.

Examples of this kind of "computer-readable storage medium" include optical mediums such as CD-ROMs (Compact Disc-ROM), magnetic storage mediums such as memory cards, and the like. Also, this kind of program can be provided by downloading via a network.

In FIG. 17, a method was described in which data for a pulse wave envelope is generated from a cuff pressure signal detected in the process of reducing the pressurizing pressure applied by the cuff 30, but one or more embodiments of the claimed invention can be similarly applied also with a method of generating data for the pulse wave envelope from a cuff pressure signal detected in the process of increasing the pressurizing pressure applied by the cuff 30.

Also, the above described a blood pressure measurement apparatus that outputs (displays on the display unit 19) a measured blood pressure value determined using the OSC method, but one or more embodiments of the claimed invention can be applied to a blood pressure measurement apparatus that outputs a measured blood pressure value determined using the K sound method as well.

For example, as in Patent Document 2, with an apparatus that calculates a measured blood pressure value using the OSC method in order to evaluate the measured blood pressure value determined using the K sound method, it is possible to determine whether or not there is blood pressure variation using the above-described method and correct the pulse wave envelope according to the determination result, and thereby determine the measured blood pressure value.

Also, in FIG. 2, the microphone 23 was described as being in the main body portion 10, but a configuration is possible in which the microphone 23 is provided in the cuff 30.

As described above, the present specification discloses the following items.

According to one or more embodiments of the claimed invention, the disclosed blood pressure measurement apparatus includes: a cuff configured to be attached at a measurement site of a body; a pressurizing pressure adjustment unit configured to change a pressurizing pressure applied by the cuff to the measurement site; a pressure detection unit configured to detect pressure in the cuff during a period of changing the pressurizing pressure; a pulse wave detection unit configured to detect pulse waves in a cuff pressure signal that is a signal output from the pressure detection unit, the pulse waves being pressure components superimposed on the pressurizing pressure in synchronization with the body's pulse; a blood flow sound detection unit configured to detect blood flow sounds that occur during a period of changing the pressurizing pressure; a pulse wave envelope data generation unit configured to generate data for a pulse wave envelope that associates amplitude values of the pulse waves detected by the pulse wave detection unit with the pressurizing pressures at times when the pulse waves were generated; a blood pressure determination unit configured to determine a measured blood pressure value using the data for the pulse wave envelope; a blood flow sound envelope data generation unit configured to generate data for a blood flow sound envelope that associates amplitude values of blood flow sound signals, which are signals output from the blood flow sound detection unit, with the pressurizing pressures at times when the blood flow sound signals were generated; a blood pressure variation determination unit configured to use the data for the pulse wave envelope and the data for the blood flow sound envelope to determine whether or not there is periodic variation in the blood pressure during the period of changing the pressurizing pressure; and a control unit configured to perform control according to the determination result of the blood pressure variation determination unit.

According to one or more embodiments of the claimed invention, the disclosed blood pressure measurement apparatus is such that if it is determined by the blood pressure variation determination unit that there is periodic variation in the blood pressure, the control unit corrects the data for the pulse wave envelope in accordance with the shape of the pulse wave envelope, and if it is determined by the blood pressure variation determination unit that there is periodic variation in the blood pressure, the blood pressure determination unit uses the data for the pulse wave envelope, which was corrected by the control unit, to determine the measured blood pressure value.

According to one or more embodiments of the claimed invention, the disclosed blood pressure measurement apparatus is such that if the pulse wave envelope has a shape with a plurality of peak portions or a trapezoidal shape that rises accompanying an increase in the pressurizing pressure, subsequently flattens, and falls thereafter, and the blood flow sound envelope has a shape with a plurality of peak portions, the blood pressure variation determination unit determines that there is periodic variation in the blood pressure.

According to one or more embodiments of the claimed invention, the disclosed blood pressure measurement apparatus is such that if it is determined by the blood pressure variation determination unit that there is periodic variation in the blood pressure and the pulse wave envelope has a shape with a plurality of peak portions, the control unit deletes amplitude values other than those of a portion of a pulse wave envelope extending from the highest peak portion of the plurality of peak portions to an adjacent trough portion, and in place of the deleted amplitude values, interpolates new amplitude values according to the shape of the pulse wave envelope that was deleted.

According to one or more embodiments of the claimed invention, the disclosed blood pressure measurement apparatus is such that if it is determined by the blood pressure variation determination unit that there is periodic variation in the blood pressure and the pulse wave envelope has the trapezoidal shape, the control unit deletes amplitude values of the flat portion of the pulse wave envelope, and in place of the deleted amplitude values, interpolates new amplitude values according to the shape of the pulse wave amplitude envelope outside of the flat portion.

According to one or more embodiments of the claimed invention, the disclosed blood pressure measurement apparatus is such that the control unit outputs information indicating the determination result of the blood pressure variation determination unit.

According to one or more embodiments of the claimed invention, the disclosed blood pressure measurement method includes: a pulse wave detection step of detecting pulse waves in a pressure signal of a cuff attached at a measurement site of a body, the pressure signal being detected during a period of reducing a pressurizing pressure applied by the cuff to the measurement site, the pulse waves being pressure components superimposed on the pressurizing pressure in synchronization with the body's pulse; a blood flow sound acquiring step of acquiring blood flow sound signals corresponding to blood flow sounds that occur during a period of changing the pressurizing pressure; a pulse wave envelope data generation step of generating data for a pulse wave envelope that associates amplitude values of the pulse waves detected in the pulse wave detection step with the pressurizing pressures at times when the pulse waves were generated; a blood pressure determination step of determining a measured blood pressure value using the data for the pulse wave envelope; a blood flow sound envelope data generation step of generating data for a blood flow sound envelope that associates amplitude values of the blood flow sound signals acquired in the blood flow sound acquiring step with the pressurizing pressures at times when the blood flow sound signals were generated; a blood pressure variation determination step of using the data for the pulse wave envelope and the data for the blood flow sound envelope to determine whether or not there is periodic variation in the blood pressure during the period of changing the pressurizing pressure; and a control step of performing control according to the determination result of the blood pressure variation determination step.

According to one or more embodiments of the claimed invention, the disclosed blood pressure measurement program is a program configured to cause a computer to execute the steps of the blood pressure measurement method.

One or more embodiments of the claimed invention can be applied to a blood pressure meter for home use, for example, and is useful for managing the health of a user.

Although one or more embodiments of the claimed invention have been described in detail and with reference to specific embodiments, it is apparent to a person skilled in the art that various modifications and amendments can be added without straying from the spirit and scope of the present invention. This application claims the benefit of Japanese Patent Application No. 2012-217408, filed Sep. 28, 2012, which is hereby incorporated by reference herein in its entirety.

REFERENCE NUMERALS LIST

1 Blood pressure measurement apparatus
10 Main body portion
11 Pressure sensor
18 CPU
22 Memory
23 Microphone
30 Cuff
181 Pulse wave detection unit
182 K sound detection unit
183 Pulse wave envelope generation unit
184 K sound envelope generation unit
185 Blood pressure variation determination unit
186 Pulse wave envelope correction unit
187 Blood pressure determination unit
188 Blood pressure output unit

The invention claimed is:

1. A blood pressure measurement apparatus comprising:
a cuff configured to be attached at a measurement site of a body;
a pressurizing pressure adjustment unit configured to change a pressurizing pressure applied by the cuff to the measurement site;
a pressure detection unit that detects pressure in the cuff during a period of changing the pressurizing pressure;
a pulse wave detection unit that detects pulse waves in a cuff pressure signal that is a signal output from the pressure detection unit, the pulse waves being pressure components superimposed on the pressurizing pressure in synchronization with the body's pulse;
a blood flow sound detection unit that detects blood flow sounds that occur during a period of changing the pressurizing pressure;
a pulse wave envelope data generation unit that generates data for a pulse wave envelope that associates amplitude values of the pulse waves detected by the pulse wave detection unit with the pressurizing pressures at times when the pulse waves were generated;
a blood pressure determination unit that determines a measured blood pressure value using the data for the pulse wave envelope;

a blood flow sound envelope data generation unit that generates data for a blood flow sound envelope that associates amplitude values of blood flow sound signals, which are signals output from the blood flow sound detection unit, with the pressurizing pressures at times when the blood flow sounds were generated;

a blood pressure variation determination unit that uses the data for the pulse wave envelope and the data for the blood flow sound envelope to determine whether or not there is periodic variation in the blood pressure during the period of changing the pressurizing pressure; and a control unit that performs control according to the determination result of the blood pressure variation determination unit, wherein if it is determined by the blood pressure variation determination unit that there is periodic variation in the blood pressure, the control unit corrects the data for the pulse wave envelope in accordance with the shape of the pulse wave envelope, wherein if it is determined by the blood pressure variation determination unit that there is periodic variation in the blood pressure, the blood pressure determination unit uses the data for the pulse wave envelope, which was corrected by the control unit, to determine the measured blood pressure value, wherein if the pulse wave envelope has a shape with a plurality of peak portions or a trapezoidal shape that rises accompanying an increase in the pressurizing pressure, subsequently flattens, and falls thereafter, and the blood flow sound envelope has a shape with a plurality of peak portions, each of the peak portions being determined based on peak amplitude values greater than trough amplitude values of adjacent trough portions by a threshold value, the blood pressure variation determination unit determines that there is periodic variation in the blood pressure, and wherein the periodic variation is respiratory variation.

2. The blood pressure measurement apparatus according to claim 1, wherein if it is determined by the blood pressure variation determination unit that there is periodic variation in the blood pressure and the pulse wave envelope has a shape with a plurality of peak portions, the control unit deletes amplitude values other than those of a portion of the pulse wave envelope extending from the highest peak portion of the plurality of peak portions to an adjacent trough portion, and in place of the deleted amplitude values, interpolates new amplitude values according to the shape of the pulse wave envelope that was deleted.

3. The blood pressure measurement apparatus according to claim 1, wherein if it is determined by the blood pressure variation determination unit that there is periodic variation in the blood pressure and the pulse wave envelope has the trapezoidal shape, the control unit deletes amplitude values of the flat portion of the pulse wave envelope, and in place of the deleted amplitude values, interpolates new amplitude values according to the shape of the pulse wave amplitude envelope outside of the flat portion.

4. The blood pressure measurement apparatus according to claim 1, wherein the control unit outputs information indicating the determination result of the blood pressure variation determination unit.

5. The blood pressure measurement apparatus according to claim 1, wherein the control unit outputs information indicating the determination result of the blood pressure variation determination unit.

6. The blood pressure measurement apparatus according to claim 2, wherein the control unit outputs information indicating the determination result of the blood pressure variation determination unit.

7. The blood pressure measurement apparatus according to claim 3, wherein the control unit outputs information indicating the determination result of the blood pressure variation determination unit.

8. A blood pressure measurement method comprising:

a pulse wave detection step of detecting pulse waves in a pressure signal of a cuff configured to be attached at a measurement site of a body, the pressure signal being detected during a period of reducing a pressurizing pressure applied by the cuff to the measurement site, the pulse waves being pressure components superimposed on the pressurizing pressure in synchronization with the body's pulse;

a blood flow sound acquiring step of acquiring blood flow sound signals corresponding to blood flow sounds that occur during a period of changing the pressurizing pressure;

a pulse wave envelope data generation step of generating data for a pulse wave envelope that associates amplitude values of the pulse waves detected in the pulse wave detection step with the pressurizing pressures at times when the pulse waves were generated;

a blood pressure determination step of determining a measured blood pressure value using the data for the pulse wave envelope;

a blood flow sound envelope data generation step of generating data for a blood flow sound envelope that associates amplitude values of the blood flow sound signals acquired in the blood flow sound acquiring step with the pressurizing pressures at times when the blood flow sound signals were generated;

a blood pressure variation determination step of using the data for the pulse wave envelope and the data for the blood flow sound envelope to determine whether or not there is periodic variation in the blood pressure during the period of changing the pressurizing pressure; and a control step of performing control according to the determination result of the blood pressure variation determination step, wherein if it is determined in the blood pressure variation determination step that there is periodic variation in the blood pressure, the control step corrects the data for the pulse wave envelope in accordance with the shape of the pulse wave envelope, wherein if it is determined in the blood pressure variation determination step that there is periodic variation in the blood pressure, in the blood pressure determination step, the data for the pulse wave envelope, which was corrected in the control step, is used to determine the measured blood pressure value, wherein if the pulse wave envelope has a shape with a plurality of peak portions or a trapezoidal shape that rises accompanying an increase in the pressurizing pressure, subsequently flattens, and falls thereafter, and the blood flow sound envelope has a shape with a plurality of peak portions, each of the peak portions being determined based on peak amplitude values greater than trough amplitude values of adjacent trough portions by a threshold value, the blood pressure variation determination unit determines that there is periodic variation in the blood pressure, and wherein the periodic variation is respiratory variation.

9. A non-transitory computer readable medium having stored thereon a blood pressure measurement program configured to cause a computer to execute the steps of the blood pressure measurement method according to claim 8.

* * * * *